United States Patent [19]

Marzolf et al.

[11] Patent Number: 4,615,341
[45] Date of Patent: Oct. 7, 1986

[54] SYRINGE DEVICE FOR PHYSIOLOGICAL FLUID SAMPLING

[75] Inventors: Willis L. Marzolf, Stockton, Calif.; Michael H. Snyder, Reno, Nev.

[73] Assignee: Syringe Industries, Inc., Greenwhich, Conn.

[21] Appl. No.: 274,811

[22] Filed: Jun. 18, 1981

[51] Int. Cl.[4] .............................................. A61B 5/00
[52] U.S. Cl. ..................................... 128/765; 604/231
[58] Field of Search ................ 128/763, 768, 765, 766

[56] References Cited

U.S. PATENT DOCUMENTS

| | | | |
|---|---|---|---|
| 3,216,616 | 11/1965 | Blankenship | 222/47 |
| 3,623,475 | 11/1971 | Sanz | 128/162 |
| 3,943,917 | 3/1976 | Johansen | 128/763 |
| 3,960,139 | 6/1976 | Bailey | 128/762 |
| 4,020,831 | 5/1977 | Adler | 128/765 |
| 4,133,304 | 1/1979 | Bailey | 128/764 |
| 4,206,768 | 6/1980 | Bailey | 128/763 |
| 4,299,238 | 11/1981 | Baidwan et al. | 128/763 |

Primary Examiner—Edward M. Coven
Assistant Examiner—Max F. Hindenburg
Attorney, Agent, or Firm—Timothy J. Martin

[57] ABSTRACT

A physiological fluid sampling device connectable to a hypodermic needle has a sampling chamber of selectably variable volume defined by a sealing member in the form of a piston which is manually movable in a housing member due to its attachment to a plunger extending out of the housing member. The chamber is formed by a closed end of the housing, the housing side wall, and the sealing member, and a bore through the housing end wall permits fluid communication with the needle. The sealing member forms a constant hermetic seal around the housing side wall, but contaminant gases may escape from the chamber through exhaust passageways formed in the sealing member. Each of these passageways contains liquid reactive material so that they automatically seal upon contact with a physiological fluid, such as blood, to prevent re-entry of contaminant gases. Crystalline heparin coats the interior surface of the housing member to stop clotting of arterial blood.

21 Claims, 18 Drawing Figures

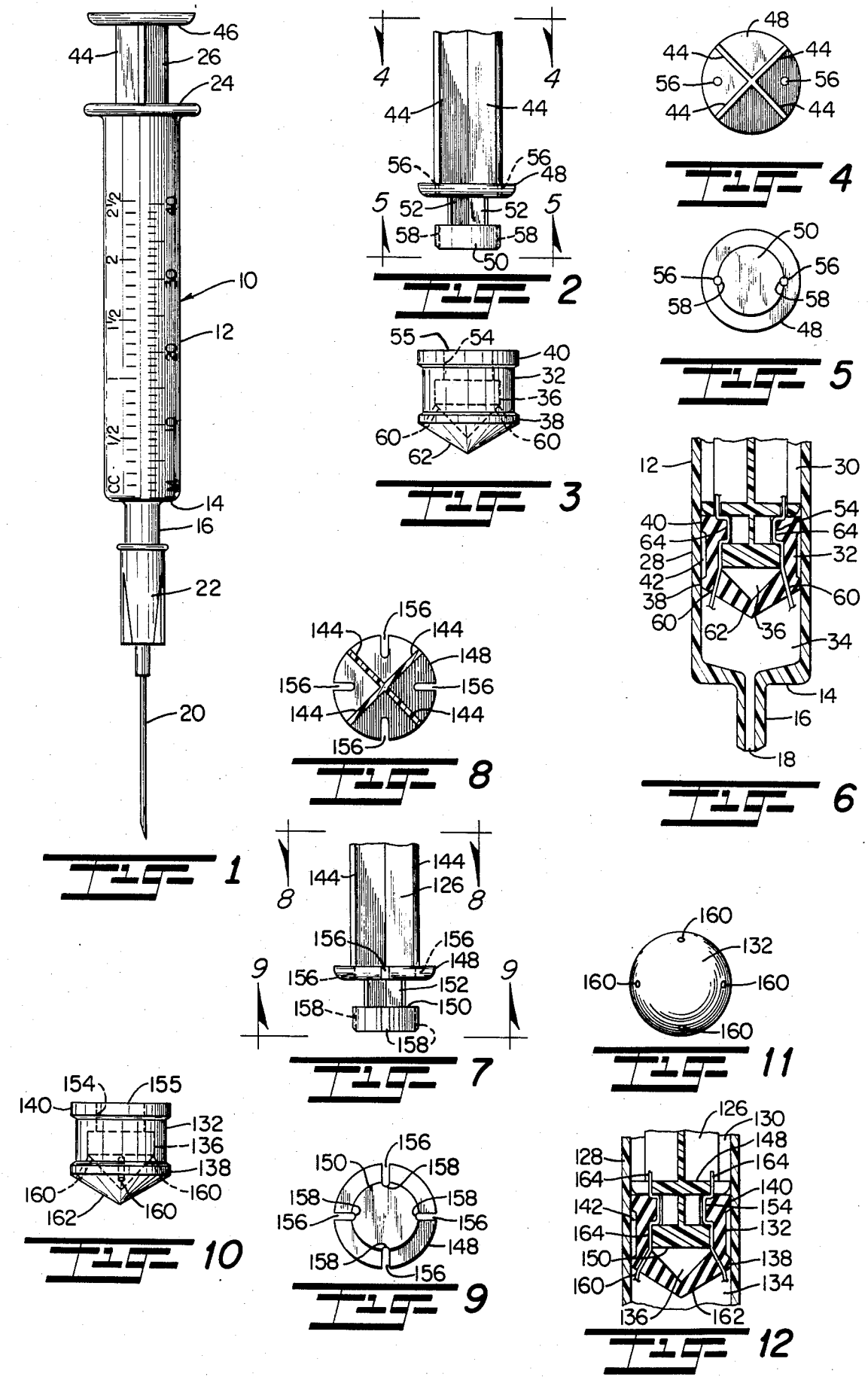

SYRINGE DEVICE FOR PHYSIOLOGICAL FLUID SAMPLING

BACKGROUND OF THE INVENTION

This invention relates to a device for collecting a sample of physiological fluid such as a blood sample so that subsequent analysis may be made for diagnostic purposes. In many such applications, including blood pH and blood gas analysis, it is desirable that the sample be taken in a manner wherein potentially contaminating gases contained in the device are removed while the sample is taken. The present invention incorporates structure to vent unwanted gases and at the same time is configured to be adaptable for use with various analytical laboratory machines in order to avoid the necessity of transferring the sample from one container to another prior to analysis. Accordingly, the sampling device according to the present invention provides a means for selectively isolating a blood sample from contaminant gases.

As noted, the present invention is useful in blood gas analysis and is constructed specifically to enhance the ease and accuracy of this process. The value of blood gas analysis has long been recognized by the medical community, but several problems have been present in utilizing blood gas analysis as a diagnostic tool. Such analysis requires a sample of known volume which is pure from contaminants which would render the results of the analysis suspect. Typical contaminants which often introduce error in analysis are atmospheric air, other gases or fluids, and some solids materials. Isolation of the sample from these contaminants is therefore crucial. Where a blood sample is taken and is subsequently transferred from one container to another prior to analysis, there is an increased chance for introduction of these contaminants. Thus, it is desirable that the analysis take place with the blood remaining in the sampling cartridge.

Another problem that has been confronted in blood gas analysis, which typically requires arterially collected blood, is that the blood cannot be permitted to clot. To this end, prior art devices have preconditioned the container into which the blood sample is received with an anti-coagulant solution although the dilutent of the solution may, itself, cause contamination of the sample. Some prior art techniques include the introduction of crystalline heparin whether as a single crystal or as a crystalline coating on the interior wall of the cartridge so that this problem is alleviated.

The prior art has recognized these problems and has proposed various structures to minimize them. For example, U.S. Pat. No. 4,133,304, issued Jan. 9, 1979 to EMDE Corporation, the assignee of the present invention, discloses an apparatus which permits the collection of a blood sample so that it is isolated within a capillary cartridge of standard volume with this cartridge being coated with a crystalline heparin to prevent clotting of the blood sample. As the sample is drawn into the cartridge through a hypodermic needle, contaminant gases which may be present in the cartridge are vented through the opposite end of the cartridge which is sealed by a resilient member but through which a fiber extends to provide an exhaust passageway for the gas. When the capillary cartridge is filled, the technician removes the fiber so that the resilient seal collapses to seal the blood sample within the cartridge. While this is an exceptionally good device for taking the sample, it has a restriction in that only one sample volume may be obtained so that several different sizes of the sampling device must be produced and stocked to provide versatility of sample volumes.

Another device which uses crystalline heparin is described in U.S. Pat. No. 4,206,768, issued June 10, 1980. This syringe device is similar to a standard hypodermic syringe, having a piston-like sealing member positioned in a cylindrical body and a plunger connected to this sealing member. The only departure of this device from the standard syringe is the provision of a plastic thread which is connected to the plunger and which extends between the wall of the main body of the syringe and the sealing member so as to break the hermetic seal therebetween. This device allows the plunger to be set at a required volume, and, as blood fills the syringe, contaminant gases escape through the broken seal between the side wall of the syringe and the sealing member. When the syringe is filled with blood, the plunger is rotated to withdraw the thread so that a seal may be re-established. Several problems have been noted in this device, however, in that operation requires a fairly complex procedure, including the alignment of the hypodermic needle bevel with the plastic line breaking the seal of the sealing member. An additional problem results in the leakage of blood through the broken seal portion both while the line is in place and after the withdrawal of the plastic line.

Therefore, it is desirable to provide an apparatus which permits the collecting of samples of various selected volumes by a single unit while at the same time isolating the sample from contaminants without leakage. The present device accomplishes this by having a movable sealing member through which contaminant gases may escape but which automatically seals upon contact with a liquid such as blood or other physiological fluid.

SUMMARY OF THE INVENTION

It is an object of the present invention to provide a device for sampling physiological fluids, such as blood, wherein contaminant gases are vented from the sampling chamber as a sample is taken.

It is another object of the present invention to provide a device for sampling physiological fluids such as blood wherein a sample of a variable pre-selected volume may be collected and which automatically seals upon contact with the physiological fluid after contaminant gases are removed from the sampling device.

It is yet another object of the present invention to provide a device for collection of physiological fluids wherein a chamber of varying volume is defined by a movable sealing member through which contaminant gases may be exhausted yet which seals against re-entry of those gases upon contact with the physiological fluid.

A still further object of the present invention is to provide for the collection of arterial blood by means of a device wherein contaminant gases are automatically expelled from a collection chamber of variable volume which is insensitive to rotational orientation and which includes an anti-coagulant to prevent clotting of the arterial blood.

To accomplish these and other objects, the present invention broadly includes a housing member or main body having one end mateable with a hypodermic needle and in fluid communication with the needle. A movable end wall is mounted in the interior of the housing member so that it may be positioned to define a chamber of pre-selected but variable volume. Sealing means is associated with the end wall for maintaining an hermetic seal completely around its perimeter against the interior side wall of the housing member. One or more exhaust passageways are formed in the movable end wall with these passageways containing a liquid reactive material which will substantially seal the passageways on contact with a liquid. When the sample is being drawn, fluids in the form of gaseous contaminants are evacuated through the passageways, but, as the liquid blood comes in contact with the end wall and its associated passageways, the liquid reactive means in the passageway seals the passageway so as to prevent contaminant gases from re-entering the chamber to contaminate the blood sample. In this manner, a pure sample is obtained.

In the preferred embodiment of the present invention, the main housing member is cylindrical in shape and closed at one end except for an axial bore extending through the closed end. An attachment means such as an axially projecting nub is provided on the exterior of the closed end so that a hypodermic needle may be attached thereto with the hypodermic needle being in fluid communication with the interior of the housing member. The movable end wall is defined by a cup-shaped member which receives the tip of a plunger, and the sealing member-plunger assembly is placed axially in the housing member. The plunger extends through an opening in the housing member opposite its closed end to be exteriorly accessible to the user of the device. Since the plunger is manually movable, an operator can selectively position the sealing member to adjust the volume of the sample chamber which is defined by the end wall of the sealing member and the closed end wall of the housing member.

In order to vent contaminant gases, a plurality of passageways extend longitudinally through the sealing member so that the chamber of variable volume communicates with the external atmosphere. The passageways are equiangularly spaced around the common longitudinal axis of the sealing member and the housing member. A liquid reactive material, such as a hydrophilic fiber, completely fills each of the passageways so that, upon contact with a liquid, the fibers swell to substantially seal the passageways.

In operation, the hypodermic needle is attached to the syringe device, the sealing member is adjusted for the desired volume, and the needle inserted into the body. As the sample fluid fills the chamber of variable volume, unwanted gases are expelled through the passageways past the fibrous materials so that they may exit the chamber. However, as the liquid sample comes in contact with the fibrous material in the passageways, the passageways are sealed by the swelling of the fibers so that gases may not re-enter the chamber to contaminate the sample fluid. By providing a plurality of exhaust passageways, and preferably three or more such passageways, the effect of the rotational orientation of the sealing member is minmized since there will always be one passageway oriented near the extreme vertical portion of that chamber when the housing member is at a small angle to the horizon.

Other objects, advantages and features of the present invention will become more readily appreciated and understood when taken together with the following detailed description in conjunction with the accompanying drawings in which:

BRIEF DESCRIPTION OF THE DRAWINGS

FIG. 1 is a side view in elevation of the physiological fluid sampling device according to the preferred embodiment of the present invention;

FIG. 2 is a side view in elevation of the interior tip of the plunger member according to the preferred embodiment of the present invention;

FIG. 3 is a side view in elevation of the sealing member according to the preferred embodiment of the present invention;

FIG. 4 is a cross-sectional view of the plunger member taken about lines 4—4 of FIG. 2;

FIG. 5 is a bottom-plan view of the plunger member taken about lines 5—5 of FIG. 2;

FIG. 6 is a cross-sectional view of the preferred embodiment of the present invention showing the sealing member and plunger tip mounted in the housing member according to the preferred embodiment of the present invention;

FIG. 7 is a side view in elevation of the first alternate embodiment of the plunger tip of the present invention;

FIG. 8 is a cross-sectional view taken about lines 8—8 of FIG. 7;

FIG. 9 is a bottom-plan view taken about lines 9—9 of FIG. 7;

FIG. 10 is a side view in elevation of the first alternate embodiment of the sealing member of the present invention;

FIG. 11 is a bottom-plan view of the sealing member shown in FIG. 10;

FIG. 12 is a side view in cross-section showing the plunger tip and sealing member of the first alternate embodiment of the present invention mounted in the housing member;

DETAILED DESCRIPTION OF THE PREFERRED EMBODIMENT

Figure 13:
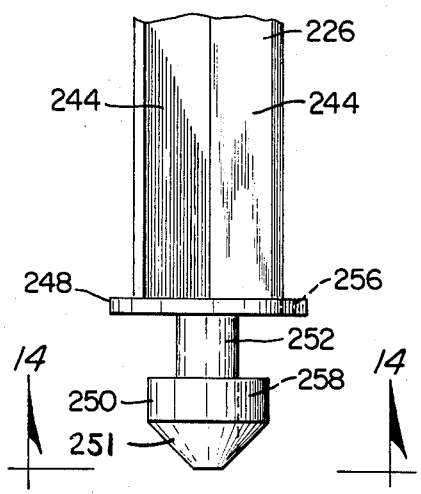
FIG. 13 is a side-plan view of a plunger tip according to a second alternate embodiment of the present invention.
Figure 14:
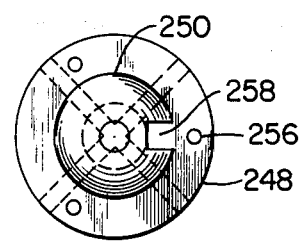
FIG. 14 is a bottom-plan view taken about line 14—14 of FIG. 13.

The present invention is directed to a device or apparatus for sampling physiological fluids and is particularly useful for sampling arterial blood for purposes of providing a specimen for arterial blood gas analysis and blood pH analysis. It should be appreciated, however, that the present invention is suitable for collecting other types of physiological specimens and is not limited to the sampling of arterial blood. The sampling is done so that a pre-selected volume of blood is received by the device, although this volume is variable according to the preferred embodiment of the present invention, with unwanted contaminant gases being vented from the device as the sample is taken in order to obtain a pure sample for analysis.

The preferred embodiment of the present invention is shown in FIG. 1 wherein sampling device 10 has a main housing 12, constructed of glass or plastic, which is graduated in units of volume as is known in the medical art. One end of housing 12 is substantially closed by end wall 14, and a nub 16 is provided to attach a hypodermic needle 20 housing 12 in fluid communication with the interior thereof. Specifically, hypodermic needle 20 to has a sleeve 22 which receives nub 16 so that fluid entering the hypodermic needle can pass through bore 18 into the interior of housing 12. Housing 12 is provided with an open end 24 opposite end wall 14, and a plunger 26 extends through opening 24 so that it has a portion positioned exteriorly of housing 12 with plunger 26 being axially movable into and out of housing 12. Preferably, housing 12 is cylindrical with a surrounding side wall 28 which is coated with sodium or lithium heparin in crystalline form to prevent blood clotting as discussed in U.S. Pat. No. 4,133,304. End wall 14 and side wall 28 define an open cavity 30 in the interior of housing 12. Plunger 26 extends, therefore, into this cavity. A piston member 32 is mounted in cavity 30 and is axially slidable in housing 12. Accordingly, piston member 32 divides cavity 30 to define a chamber 34. Chamber 34 thus has a variable volume depending upon the selectable axial position of piston member 32 in cavity 30.

Preferrably, piston member 32 is formed of a resilient material, such as rubber, in a generally cylindrical configuration and acts as a sealing member for chamber 34. A cavity 36, having a mouth 55, is formed in the interior of piston member 32 to receive an end portion or mounting member 50 of plunger 26. Piston member 32 has a pair of radially outwardly extending shoulders 38 and 40. When piston member 32 is positioned within cavity 30, shoulders 38 and 40 abut side wall 28 on the interior of housing 12 completely around the perimeter of piston member 32 to form an hermetic seal between piston member 32 and side wall 28. Since shoulders 38 and 40 project radially outwardly from the main body of piston member 32, a small chamber 42 is defined between the piston member 32 and side wall 28 with chamber 42 being in the shape of a cylindrical shell.

The construction of plunger 26 is shown in greater detail in FIGS. 2, 4 and 5 wherein it should be appreciated that plunger 26, in the preferred embodiment, is formed of a plastic material and has an elongated main body which terminates at one end in a flat disc 46 and at the opposite end in a flat disc 48, which is slightly smaller than disc 46. The main body of plunger 26 is formed of four vanes 44 which are connected at a common longitudinal edge and which extend radially outwardly at right angles to one another. Discs 46 and 48 are thus perpendicular to the longitudinal axis of plunger 26 defined by the junction of vanes 44. A mounting member 50 in the form of a flat circular plate is mounted to a disc 48 by means of four smaller vanes 52 which extend radially outwardly from the common longitudinal axis of vanes 44. Mounting member 50 is oriented generally parallel to disc 48 and serves to mount piston member 32 to the end of plunger 26. Specifically, mounting member 50 is mateably received by cavity 36 formed in piston member 32 and is resiliently retained thereon by means of a radially inwardly projecting shoulder 54 which surrounds the interior surface of cavity 36 of piston 32 adjacent shoulder 40. Accordingly, shoulder 55 has an axial thickness slightly smaller than the length of vanes 52, and cavity 36 is shaped to conveniently receive mounting member 50.

From the above, it should be appreciated that piston member 32 is axially movable within cavity 30 by means of manual operation of plunger 26 Thus, a chamber 34 of variable volume is formed, as noted, and shoulders 38 and 40 always remain in an hermetically sealed relationship with the interior surface of side wall 38.

As a physiological fluid enters chamber 34 it is desirable that contaminant gases be permitted to exit chamber 34. To this end, at least one exhaust passageway is provided through piston member 32 and around the end of plunger 26 as defined by plate 50, vanes 52, and disc 48. Specifically, in the preferred embodiment, a pair of exhaust passageways are formed for venting contaminant gases from chamber 34. Since these passageways are formed through the resilient piston member, the sidewalls of the passageways are flexible and can thus collapse to close the passageways. As is shown in FIGS. 2, 4, and 5, disc 48 has a pair of holes 56 positioned 180° apart and plate 50 has a pair of channels 58 formed longitudinally in its circumferential edge so that each channel 58 is respectively aligned with a hole 56. Piston member 32 has a pair of ports 60 formed in its end wall 62 in communication with cavity 36. Accordingly, chamber 34 is in fluid communication with cavity 30 so that contaminant gases may pass through port 60 into cavity 36 after which they may pass through channels 58 around plate 50. The gases are then vented to the external atmosphere by passing through holes 56 formed in disc 48 and into cavity 30.

Since it is important, for the scope of this invention, that contaminant gases not be permitted to re-enter chamber 34 after it is filled with the physiological fluid, it is necessary that the exhaust passageways be sealable upon the filling of chamber 34 with the fluid, which, in the case of physiological fluids, is in the form of a liquid material, such as blood. To this end, a liquid reactive material is positioned in the fluid passageways, which material reacts on contact with liquid to substantially seal the passageways. In the preferred embodiment of the present invention, the liquid reactive material is defined by a thread 64 which is positioned in each of these passageways. Thread 64 can be constructed of any hydrophilic material, such as cotton or other materials known in the art. As may be seen in FIG. 6, a pair of threads 64 are each mounted to extend between cavity 30 and chamber 34. In so doing, each thread 64 extends through a respective hole 56, around shoulder 64 and through a respective channel 58 so that it may then pass through port 60 in end wall 62 to terminate in chamber 34. Thus, each thread 64 completely bypasses the plunger tip to enable the venting of gases from chamber 34. Each thread 64 performs a dual function. First, each thread 64 acts to maintain its respective port 60 open and to provide a gas vent path. Second, upon contact with the liquid blood, the fibrous thread swells to seal ports 60, and, correspondingly, end wall 62 is sealed to prevent re-entry of contaminant gases.

The operation of the preferred embodiment of the present invention may now be more fully appreciated. Specifically, the user of sampling syringe 10, such as a doctor or other medically trained person, first connects a hypodermic needle assembly 20 and 22 to nub 16 so that hypodermic needle 20 may be inserted in the appropriate location from which the physiological fluid sample is to be taken. Plunger 26 is then manually moved so that piston 32 connected thereto is axially slid in housing 12 to a selected location corresponding to the volume of physiological fluid to be taken. This volume, of course, corresponds to the volume of chamber 34 defined by end wall 14, side wall 28 and end wall 62 which is variable depending upon the position of piston member 32 in housing 12. The hypodermic needle 20 may then be inserted into the patient's body such that the pressure of the physiological fluid will cause chamber 34 to begin filling. As chamber 34 fills with the physiological fluid in liquid form, air or other contaminant gases contained in chamber 34 are exhausted through ports 60 and around the plunger tip as described above so that they may escape through cavity 30 to the external atmosphere. Upon contact of the physiological fluid, threads 64 swell to seal ports 60 thereby preventing the re-entry of contaminant gases into chamber 34 and thus provide a pure sample of physiological fluids to be tested. The hypodermic needle 20 may then be withdrawn from the patient's body and inserted into a standard needle sealer, such as a rubber stopper (not shown) as is known in the art.

An alternate embodiment of the plunger tip assembly and the piston member is shown in FIGS. 7 through 12. While in many ways the structure shown in FIGS. 7 through 12 is similar to that discussed with respect to the preferred embodiment shown in FIGS. 1–6, this first alternate embodiment provides a different arrangement for and number of the exhaust passageways which permit the venting of gas from chamber 34 to the external environment.

Specifically, as shown in FIGS. 7, 8, and 9, plunger 126 is made up of four main vanes 144 positioned in a manner similar to that described with respect to the preferred embodiment. Plunger 126 terminates in a flat disc 148 which is oriented perpendicularly to vanes 144 and a second set of smaller vanes 152 are attached to disc 148 and support a flat mounting member 150 also in a manner similar to that described with respect to the preferred embodiment. Whereas the preferred embodiment provided a pair of holes 56 which were axially spaced 180° apart from one another, the alternate embodiment shown in FIG. 8 provides four channels 156 which are cut radially inward into the disc 148 and are spaced equiangularly around its circumference so that they are 90° apart from one another. Likewise, a plurality of channels 158 are longitudinally cut into the edge of mounting member 150 so that there is a respective channel 158 matched with a channel 156. Channels 158 correspond to channels 58 of the preferred embodiment discussed above.

Piston member 132, according to this alternate embodiment, is formed correspondingly to piston member 32 of the preferred embodiment, except that piston 132 is provided with ports 160 which are equal in number to the number of channels 156 and channels 158. Thus, in the alternate embodiment shown in FIGS. 10, 11, and 12, piston member 132 is provided with four such ports 160 which are adapted to form part of the exhaust passageways or vents for contaminant gases. The structure of piston member 132 is shown in greater detail in FIG. 10 where it should be appreciated that plunger 132 is generally cup-shaped, having a surrounding side wall and a conic nose or end wall 162 with ports 160 being drilled through end wall 162. Accordingly, piston member 132 has an internal cavity 136 with an open mouth 155 which is adapted to receive mounting member 150 in a manner described below. Piston member 132 has a pair of radially outwardly-projecting shoulders 138 and 140 which are axially spaced apart from one another and a radially inwardly projecting shoulder 154 near an end piston member 132 opposite end wall 162.

FIG. 12 shows plunger 126 and piston member 132 positioned in cylindrical housing 112 comparable to that shown in FIG. 6 of the preferred embodiment. Here, piston member 132 is mounted in housing 112 such that shoulders 138 and 140 each form an hermetic seal completely around the interior side wall of housing 112. Mounting member 150 is passed through mouth 155 and is received in cavity 136 of piston member 132 with shoulders 154 being positioned between mounting member 150 and disc 148 to resiliently retain mounting member 150 in cavity 136. Liquid reactive material in the form of a plurality of hydrophilic threads 164 extends through each port 160 and are wound through channels 158, past vanes 152, and through channels 156 to project into cavity 130 which is exposed to the external environment. In this manner, an exhaust or vent passageway is formed so that contaminant gases can pass from cavity 134 through piston member 132 and then be vented into cavity 130. Threads 164 provide a liquid reactive material such that, upon contact with physiological fluids, threads 164 will swell to seal ports 160 so that contaminant gases cannot re-enter the sample of physiological fluids so taken into chamber 134.

A third embodiment of the present invention is shown in FIGS. 13–18 with this embodiment departing in several aspects from the embodiments shown in FIGS. 1–12. Particularly, FIG. 13 shows plunger 226 comprised of four vanes 244 which are connected at a common vertex and extend radially outwardly from one another. Vanes 244 terminate in a flat disc 248 mounted at a right angle thereto, and a post 252 is axially mounted to disc 248. Post 252 supports a mounting member 250 which is generally cylindrical but which has a frustoconical nose 251. As discussed in greater detail below, disc 248 is provided with three holes 256 which are equiangularly spaced around its perimeter adjacent its edge, and mounting member 250 is provided with a channel 258 cut longitudinally therein to a depth corresponding to the radius of post 252, so that the bottom surface of channel 258 is coextensive with the surface of post 252.

Figure 17:
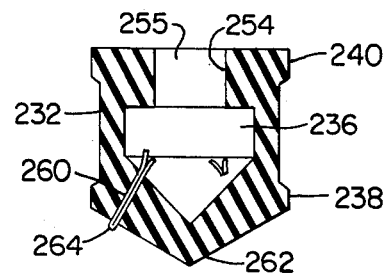
FIG. 17 is a side view and cross section of the sealing member taken about lines 17—17 of FIG. 16.
Figure 15:
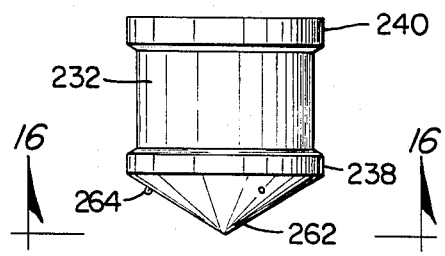
FIG. 15 is a side view in elevation of the sealing member according to the second alternate embodiment of the present invention.
Figure 16:
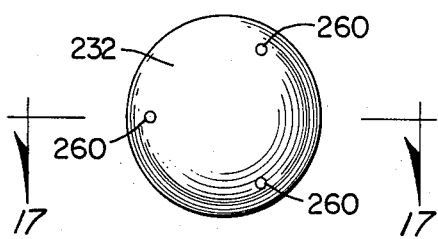
FIG. 16 is a bottom-plan view taken about line 16—16 of FIG. 15.

A piston member 232 is shown in FIGS. 15, 16, and 17, and has a generally cylindrical, cup-shaped configuration. Particularly, piston member 232 has an interior cavity 236 and a radially inwardly projecting shoulder 254 adjacent mouth 255 of cavity 236. Cavity 236 is adapted to receive mounting member 250 with shoulders 254 resiliently retaining piston member 232 on mounting member 250. Piston member 232 has a pair of radially outwardly projecting shoulders 238 and 240, which are axially spaced from one another at opposite ends of piston member 232, and a closed end wall 262 having a conic nose. Shoulder 238 is adjacent end wall 262 with shoulder 240 being at an end of piston 232 opposite end wall 262. End wall 262 is provided with three ports 260 therewith with ports 260 extending from the exterior of piston member 232 into cavity 236. Ports 260 are equiangularly spaced about the axis of piston member 232 as shown in FIG. 16 with there being three such ports 260 in this embodiment of the present invention.

Figure 18:
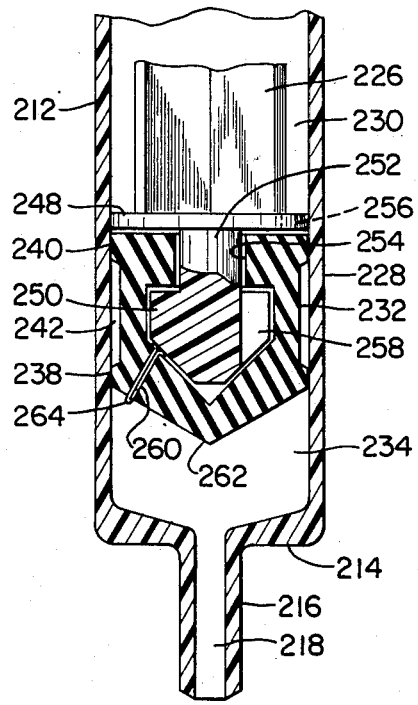
FIG. 18 is a side view in cross section of the plunger tip in sealing member mounted in the housing member according to the second alternate embodiment of the present invention.

The mounting of piston member 232 onto plunger 226 is shown in greater detail in FIG. 18 where it should be appreciated that the plunger and piston member assembly is adapted to be positioned in a generally cylindrical housing 212 in a manner similar to that described with respect to housing 12 of syringe 10 according to the preferred embodiment of the present invention. As is shown in FIG. 18, housing 212 terminates in an end wall 214 which is provided with an axially extending nub 216 which has a bore 218 therethrough. Nub 216 is adapted to secure a hypodermic needle onto end wall 214 so that fluid communication is established from the hypodermic needle through bore 218 into chamber 234 which is defined between end wall 214 of housing 212 and end wall 262 of piston member 232.

Piston member 232 is positioned to be axially slidable in housing 212 with shoulders 238 and 240 defining an hermetic seal completely around the interior side wall 228 of housing 212. Accordingly, side wall 228, shoulder 238, and shoulder 240 form a chamber 242 in the shape of a generally cylindrical shell with end wall 262 therefore defining a movable end wall for chamber 234. As noted, mounting member 250 is matably received in cavity 236 and is retained therein by means of shoulder 254 which has an axial thickness slightly smaller than the axial length of post 252 with mouth 255 having a slightly greater diameter than post 252. In this manner, the end of piston 232 adjacent shoulder 240 abuts disc 248 of plunger 226.

As is shown in FIGS. 17 and 18, ports 260 receive a thread 264 which is doubled over upon itself so that its two free ends 266 extend into cavity 236 with the folded mid-portion extending slightly outwardly from end wall 262. This configuration is desired for ease of manufacture, but accomplishes the same purpose as threads 64 and 164 of the first two embodiments of the present invention as described above. Specifically, the tip of plunger 226 defined by disc 248, post 252 and mounting member 250 are configured so that there is sufficient play to avoid a seal between piston member 232 and the tip of plunger 226. In this manner, then, three exhaust passageways are defined by ports 260, slot 258 and holes 256 so that contaminant gases may escape from chamber 234 through end wall 262 and into cavity 230 as chamber 234 fills with a sample physiological fluid. Of course, since cavity 230 is open to the external atmosphere, the contaminant gases can be released. To this end, it is necessary that there be sufficient room around the mounting member 250 and post 252 such that the gases can so escape. Notch 258 helps facilitate escape of the contaminant gases through mounting member 250. Threads 264, in a manner similar to threads 64 and 164 are formed of a liquid reactive material such that, as the physiological fluid contacts each of threads 264, each thread 264 swells to substantially seal its respective ports 260 from passage of contaminant gases so that contaminant gases may not re-enter chamber 234 once it is filled with the physiological fluid.

The operation of the sampling devices shown and described with respect to the second and third embodiments of the present invention is the same as the operation of the preferred embodiment. However, it should be appreciated that since physiological samples are often taken with the syringe 10 oriented at a small acute angle relative to the horizon and with the beveled tip of the hypodermic needle upward, it is helpful to have a sampling device that is insensitive to rotational orientation. In past devices, this orientation has been critical where only one exhaust passageway, of whatever nature, has been provided. While orientation of the ports 60 is somewhat sensitive with respect to the embodiment of the present invention shown in FIGS. 1-6, the second two embodiments substantially eliminate the problem of providing either three ports as shown in FIGS. 13-18 or four ports as shown in FIGS. 7-12 since there is always a port oriented near the uppermost portion of a respective chamber 134 or 234 regardless of the rotational positioning of the piston member in its respective housing. It should be appreciated, however, that it is within the scope of the present invention to provide any number of ports in the piston member so long as the requisite liquid reactive material be provided in those ports to substantially seal them upon contact with a physiological fluid.

Embodiments of the present invention have been shown and described with a degree of particularity to enable a complete and full understanding of those embodiments. However, it should be understood that the present invention involves inventive concepts defined in the appended claims, and these inventive concepts are not intended to be limited except insofar as the prior art requires. This physiological fluid sampling syringe may take other forms and is susceptible to various changes in detail without departing from the principles of this invention.

We claim:

1. An arterial blood sampling device adapted for use with a hypodermic needle comprising:
    a housing member including a surrounding sidewall, a stationary end wall, and an open end opposite said stationary end wall, said stationary end wall having a bore therethrough and having mounting means connected thereto for mounting a hypodermic needle to said housing member in fluid communication with said bore;
    a movable piston member including a movable end wall formed of a resilient material and facing said stationary end wall, said piston member being axially movable in said housing member whereby said sidewall, said stationary end wall and the movable end wall of said piston member define a fluid chamber of variable volume of operative to receive a blood sample, said sidewall and said piston member defining an open chamber on a side of said piston member opposite said fluid chamber, said movable end wall including passageways formed therethrough at generally equiangularly spaced intervals about the longitudinal axis of the piston member, each said passageway formed at an acute angle to said longitudinal axis and having an opening into said fluid chamber located adjacent the edge of said movable endwall;
    sealing means associated with said movable end wall for maintaining an hermetic seal between said end wall and said side wall; and
    gas permeable liquid reactive means in each of said passageways for substantially sealing its respective passageway on contact with liquid.

2. An arterial blood sampling device according to claim 1 wherein said liquid reactive means includes a hydrophilic fibrous material positioned in said passageway.

3. An arterial blood sampling device according to claim 2 wherein said liquid reactive means is a thread extending completely through each said passageway and protruding from said movable endwall into said fluid chamber.

4. An arterial blood sampling device according to claim 1 including a plunger member mounted to said piston member and extending through said open end to the exterior of said housing member in an axial direction.

5. An arterial blood sampling device according to claim 4 wherein said plunger member has a mounting on its internal end, said end wall member having a cavity formed therein for matably receiving said mounting member, said mounting member having a channel in fluid communication with said passageways.

6. An arterial blood sampling device according to claim 1 including an anti-coagulant material in said fluid chamber.

7. An arterial blood sampling device according to claim 6 wherein said surrounding sidewall interior surface is coated with said anti-coagulant material.

8. An arterial blood sampling device according to claim 1 further including a plunger member mounted to said piston member and extending exteriorly of said housing member, said housing member being cylindrical, and said piston member being generally cylindrically shaped and formed of a resilient material and having a pair of radially extending circumferential lips at opposite ends thereof, said piston member having a cavity formed in one end for matably receiving the interior end of said plunger member, said lips maintaining an hermetic seal with said housing member.

9. A syringe device adapted for use with a hypodermic needle, comprising:
a hollow body member having a surrounding sidewall, an open end and a closed end opposite said open end, said closed end having a bore therethrough and means for securing said hypodermic needle to the exterior of said body member in fluid communication with said bore;
a piston member positioned in the interior of said body member, said piston member having resilient sealing means surrounding its peripheral surface for maintaining an hermetic seal with said sidewall and being axially movable in said body member, said piston member, said sidewall and said closed end defining a fluid chamber of variable volume, said surrounding sidewall and piston member defining a second chamber on a side of said piston member opposite said fluid chamber;
a handle member extending through said open end and operatively connected to said piston member whereby said piston member may be selectable positioned axially along the interior of said body member;
said piston member having a gas vent passageway therethrough for permitting exhaust of gas from said fluid chamber through said piston member; and
liquid reactive means in said vent passageway for substantially sealing said passageway on contact with a liquid for preventing passage of liquid from said fluid chamber and for preventing reentry of gas into said fluid chamber, said liquid reactive means including a hydrophilic thread folded on itself so that it has a folded end and whereby its free ends are adjacent one another to define a second end, said thread extending a substantial distance through said passageway.

10. An arterial blood sampling device according to claim 9 wherein said piston member generally cup-shaped having an open cavity facing the open end of said body member and a closed endwall, said handle member having an exterior end adapted to be manually gripped by a user, an interior end comprising a flat plate oriented in a plane perpendicular to the longitudinal axis of said handle member, and a mounting member adapted to be matably received by said cavity and a post interconnecting said mounting member and said flat plate whereby said piston member is retained on the interior end of said handle member.

11. An arterial blood sampling device according to claim 10 wherein said gas vent passageway comprising a bore through said closed endwall, a longitudinal channel in said mounting member and an opening in said plate.

12. An arterial blood sampling device according to claim 10, there being a plurality of gas vent passageways through said piston member, each said gas vent passageway comprising a bore through said closed endwall, a longitudinal channel in said mounting member and an opening in said plate, said gas vent passageways being equiangularly spaced about the axis of said piston member.

13. An arterial blood sampling device according to claim 12 wherein said liquid reactive means in each said gas vent passageway includes a fiber thread extending through said bore in said endwall, through said channel and through said opening.

14. A syringe device according to claim 9 wherein said piston member having a cavity in a first end facing said open end, an endwall opposite said first end, and a radially inwardly projecting shoulder surrounding said cavity adjacent said first end, said handle member having a mounting member on its interior tip, said cavity receiving said mounting member whereby said shoulder resiliently retains said mounting member in said cavity.

15. An arterial blood sampling device according to claim 10 wherein said sealing means includes a pair of radially outwardly extending resilient shoulders surrounding the perimeter of said piston member at axially spaced-apart locations from one another.

16. A syringe device adapted for use with a hypodermic needle in sampling physiological fluids, comprising:
a generally tubular housing member having an open end, a closed end opposite said open end, and a surrounding sidewall having an interior and an exterior surface;
connection means on said closed end for connecting said hypodermic needle to the exterior of said housing member closed end, said closed end having a bore therethrough adapted for fluid communication with said hypodermic needle;
a plunger member extending through said open end and having a portion exterior of said housing member adapted for manual gripping and having a portion interior of said housing member terminating in a mounting member;
a piston member having a cup-shaped configuration and positioned in the interior of said housing member, said piston member having an endwall and a surrounding sidewall forming a cavity adapted to mateably receive said mounting member and having resilient sealing means on the exterior of said surrounding sidewall of the piston member for maintaining an hermetic seal between said piston member and the interior surface of said tubular housing member's surrounding sidewall;
said piston member being axially slideable in said housing member so that the surrounding sidewall and the closed end of said housing member and said endwall of said piston member define a chamber of variable volume, said endwall having a plurality of passageways found therethrough at an acute angle with respect to the longitudinal axis of said housing member and opening into the chamber of variable volume located adjacent the edge of said endwall and in fluid communication with said chamber and said cavity for permitting gases to flow between the chamber and the exterior of said housing member through said piston member; and gas permeable liquid reactive means substantially filling each said passageway for allowing flow of gases through said passageway when dry yet prohibiting flow of gases through said passageway upon contact with a liquid.

17. An arterial blood sampling device according to claim 16 wherein said liquid reactive means includes a hydrophilic fiber thread extending completely through each said passageway, each thread having a first end terminating in said chamber of variable volume and a second end terminating in said cavity.

18. An arterial blood sampling device according to claim 17 wherein said mounting member has a longitudinal channel formed therein.

19. An arterial blood sampling device according to claim 18 wherein said plunger includes a flat plate on its interior end and an axial post projecting from said plate, said mounting member attached to said post and having a larger cross-section than said post, said channel having a bottom surface coextensive with the surface of said post adjacent said channel and extending the length of said mounting member.

20. An arterial blood sampling device according to claim 19 wherein said plate has an opening therethrough.

21. An arterial blood sampling device according to claim 16 wherein said liquid reactive means includes a hydrophilic thread extending through each said passageway, each thread being folded on itself so that its free ends are adjacent one another to define a folded end terminating in said chamber of variable volume, said free ends located in said cavity.

* * * * *